(12) United States Patent
    Lee

(10) Patent No.: US 11,439,371 B2
(45) Date of Patent: Sep. 13, 2022

(54) SALIVA TEST DEVICE AND METHOD, AND ANIMAL MONITORING SYSTEM AND METHOD USING SAME

(71) Applicant: TOVSS, Taean (KR)

(72) Inventor: Joon Taik Lee, Seoul (KR)

(73) Assignee: WELLNESS FARMER CO., LTD., Cheongju-si (KR)

( * ) Notice: Subject to any disclaimer, the term of this patent is extended or adjusted under 35 U.S.C. 154(b) by 958 days.

(21) Appl. No.: 16/306,128

(22) PCT Filed: Jun. 19, 2017

(86) PCT No.: PCT/KR2017/006386
    § 371 (c)(1),
    (2) Date: Nov. 30, 2018

(87) PCT Pub. No.: WO2018/062666
    PCT Pub. Date: Apr. 5, 2018

(65) Prior Publication Data
    US 2020/0100773 A1    Apr. 2, 2020

(30) Foreign Application Priority Data
    Sep. 27, 2016 (KR) .................. 10-2016-0123963

(51) Int. Cl.
    *A61B 10/00*    (2006.01)
    *G01N 1/14*    (2006.01)
    (Continued)

(52) U.S. Cl.
    CPC ............ *A61B 10/0051* (2013.01); *A01K 7/02* (2013.01); *A61B 5/00* (2013.01); *A61B 10/00* (2013.01);
    (Continued)

(58) Field of Classification Search
    CPC .......... G01N 1/14; G01N 33/487; A01K 7/02; A01K 29/005; A61B 10/0051; A61B 5/00; A61B 10/00
    See application file for complete search history.

(56) References Cited

U.S. PATENT DOCUMENTS

2007/0062460 A1   3/2007   Simer
2012/0082955 A1*  4/2012   Yang ...................... A61C 17/06
                                                       433/91
2012/0083711 A1*  4/2012   Goldstein ............ A61B 5/4848
                                                       600/573

FOREIGN PATENT DOCUMENTS

JP    2009-128110 A    6/2009
KR    10-1716729 B1    3/2017
WO    2004-014253 A1   2/2004

* cited by examiner

*Primary Examiner* — Benjamin R Schmitt
(74) *Attorney, Agent, or Firm* — Patent Office of Dr. Chung Park

(57) ABSTRACT

A saliva test device includes: a means for generating an approach detection signal; a means for generating a contact detection signal; a drinking water supply unit for controlling the supply of drinking water in response to at least one of approach detection signals and contact detection signals; a pump for suctioning and collecting saliva in response to a contact detection signal; a test unit for testing whether a disease is present; a communication unit for informing test result information; a control unit for generating a system driving control signal in response to an approach detection signal, generating a pump driving control signal in response to a contact detection signal, generating a drinking water supply control signal in response to saliva collection, and controlling transmission of the test result information; and a memory for storing data. The saliva test device reduces animal stress and testing fees and improves productivity.

5 Claims, 8 Drawing Sheets

(51) Int. Cl.
*G01N 33/487* (2006.01)
*A61B 5/00* (2006.01)
*A01K 7/02* (2006.01)
*A01K 29/00* (2006.01)

(52) U.S. Cl.
CPC ............ *G01N 1/14* (2013.01); *G01N 33/487* (2013.01); *A01K 29/005* (2013.01); *A61B 2503/40* (2013.01)

SALIVA TEST DEVICE AND METHOD, AND ANIMAL MONITORING SYSTEM AND METHOD USING SAME

CROSS-REFERENCE TO PRIOR APPLICATIONS

This application is a national Stage Patent Application of PCT International Patent Application No. PCT/KR2017/006386, filed on Jun. 19, 2017 under 35 U.S.C. § 371, which claims priority of Korean Patent Application No. 10-2016-0123963, filed on Sep. 27, 2016, which are all hereby incorporated by reference in their entirety.

TECHNICAL FIELD

The present invention relates to a technique of testing saliva of an animal. More specifically, the present invention relates to a saliva test device and method, and an animal monitoring system and method using the same, which can collect and test saliva of an animal when the animal drinks water, and inform a result of the test.

BACKGROUND ART

Livestock and pet animals having a close relation to human life need management.

Particularly, there are disinfection rules for raised livestock, and therefore, surroundings of livestock sheds are periodically disinfected, or the livestock are vaccinated if needed.

This is for preventing infectious diseases of animals and managed by the domestic animal infectious disease control law of each country.

For example, in the case of pigs, monitoring tests are carried out three times a year in a pig farm and once a quarter in a breeding pig farm, and in the case of slaughtered pigs, farms are randomly selected to carry out the monitoring test. At this point, antibodies are detected through enzyme-linked immunosorbent serologic assay (ELISA) using serum from blood collected at the pig farms, the breeding pig farms, and slaughter houses. In addition, antigens may be detected through the ELISA diagnosis technique using white blood cells in the blood collected at the pig farms and the breeding pig farms.

The ELISA method is a method of confirming antigen-antibody reactions by combining enzymes with antibodies, and it is one of the antigen-antibody analysis methods most widely used currently since the method is simple, inexpensive and capable of mass analysis. Particularly, the method is advantageous in that it does not use radiation unlike the Radio ImmunoAssay (RIA) while being very sensitive like RIA.

Some enzymes combined with the antibody are used for a reaction of showing a color when a simple substrate solution is added, and alkaline phosphatase, Horse Radish Peroxidase (HRP) and the like are widely used as representative enzymes. These enzymes are conjugated using a chemical reaction to generated a covalent bond in the C region of an antibody molecule and are generally sold in the form of an enzyme conjugated anti-isotype antibody, e.g., alkaline phosphatase conjugated anti-mouse IgG or the like, and a user may purchase and use an enzyme conjugated antibody appropriate to the class of an antibody that the user himself uses.

The ELISA method adsorbs a protein antibody to a plastic microtiter plate to have the antibody react to an antiserum, cleanses the antibody, and adds an enzyme conjugated antiglobulin. Then, the antigen-antibody reaction is measured using a spectrophotometer on the basis of a degree of color formed by processing the substrate with the enzyme.

For example, in the case of pigs, guidelines for implementing disinfection against pig fever (cholera), which is an internationally designated malignant livestock epidemic, are announced. The pig fever is an acute fatal viral epidemic, which is very infectious and cannot be treated until present once it breaks out. Therefore, all the pigs infected or suspected to be infected are slaughtered, buried and incinerated. Furthermore, movement control is conducted in a region where the pig fever breaks out.

Although construction of a system for processing a pig fever test in real-time is required to minimize spread of infectious diseases considering the seriousness, it is insufficient yet. Meanwhile, although there is provided a method of "How to collect oral fluid samples" as a method of testing fig fever, this method has a problem of increasing stress of pigs and thus lowering productivity. In addition, fig farms avoid using the method of "How to collect oral fluid samples" due to the burden of high cost.

Therefore, there is a need of inexpensive test method, while being capable of processing the test in real-time.

DISCLOSURE OF INVENTION

Technical Problem

Therefore, the present invention has been made in view of the above problems, and it is an object of the present invention to provide a saliva test device and method, and an animal monitoring system and method using the same, which can collect saliva of a corresponding animal when the animal drinks water, test occurrence of a disease in real-time, and inform a management center of test result information.

Technical Solution

To accomplish the above object, according to one aspect of the present invention, there is provided a saliva test device comprising: a means for generating an approach detection signal; a means for generating a contact detection signal; a drinking water supply unit for controlling supply of drinking water in response to at least any one of a plurality of approach detection signals and contact detection signals; a pump connected to one end of a tube installed at an end portion of a drinking water pipe to suction and collect saliva in response to the contact detection signal; a test unit for performing a disease occurrence test on the collected saliva and outputting test result information; a communication unit for informing a management center of the test result information; a control unit for generating a system driving control signal in response to the approach detection signal, generating a pump driving control signal in response to the contact detection signal, generating a drinking water supply control signal in response to collection of the saliva, and performing transmission control on the test result information; and a memory for storing an operation program and storing inputted and outputted data.

At this point, the test unit preferably includes: a saliva storage unit connected to the other end of the tube to store the collected saliva; a saliva supply unit for supplying the stored saliva; a test module for performing a disease occurrence test; and a saliva discharge unit for discharging the saliva.

In addition, a peristaltic tubing pump is preferably used as the pump.

According to another aspect of the present invention, there is provided a saliva test method comprising the steps of: driving a system in response to generation of an approach detection signal; collecting saliva in the mouth of a corresponding animal by driving a peristaltic tubing pump in response to generation of a contact detection signal; generating a peristaltic tubing pump drive stop signal and a drinking water supply control signal and providing drinking water when the collected saliva reaches a predetermined amount; supplying the collected saliva to a test unit and performing a disease occurrence test in real-time; generating and outputting test result information of the disease occurrence test; and informing a management center of the test result information.

Here, a solenoid valve installed in the drinking water pipe is preferably opened in response to the drinking water supply control signal.

An animal monitoring system of the present invention comprises: a chip installed in an animal; a saliva test device installed in a water supply facility to collect saliva from the animal, test occurrence of a disease from the collected saliva in real-time, and transmit test result information to a management center; and the management center for receiving and managing the test result information.

An animal monitoring method of the present invention comprises the steps, performed by a saliva test device, of: (a) detecting use of a water supply facility by an animal having a chip installed therein, collecting saliva, and performing a disease occurrence test on the collected saliva in real-time; and (b) informing a management center of test result information of the disease occurrence test.

At this point, a disease occurrence analysis time is confirmed for each entity, and when an entity, the disease occurrence analysis time of which does not exceeds a set time, approaches, the peristaltic tubing pump preferably maintains a stopped state, and if the contact detection signal is generated, drinking water is preferably supplied at once.

Advantageous Effects

As described above, according to the saliva test device and method of the present invention, and the animal monitoring system and method using the same, since stress of an animal can be reduced through a simple test method, improvement of productivity can be expected, and testing fees can be minimized.

In addition, according to the present invention, since real-time monitoring is possible for each entity, it is possible to promptly respond when a disease occurs, and an entity having a disease can be accurately identified.

BEST MODE FOR CARRYING OUT THE INVENTION

Figure 1:
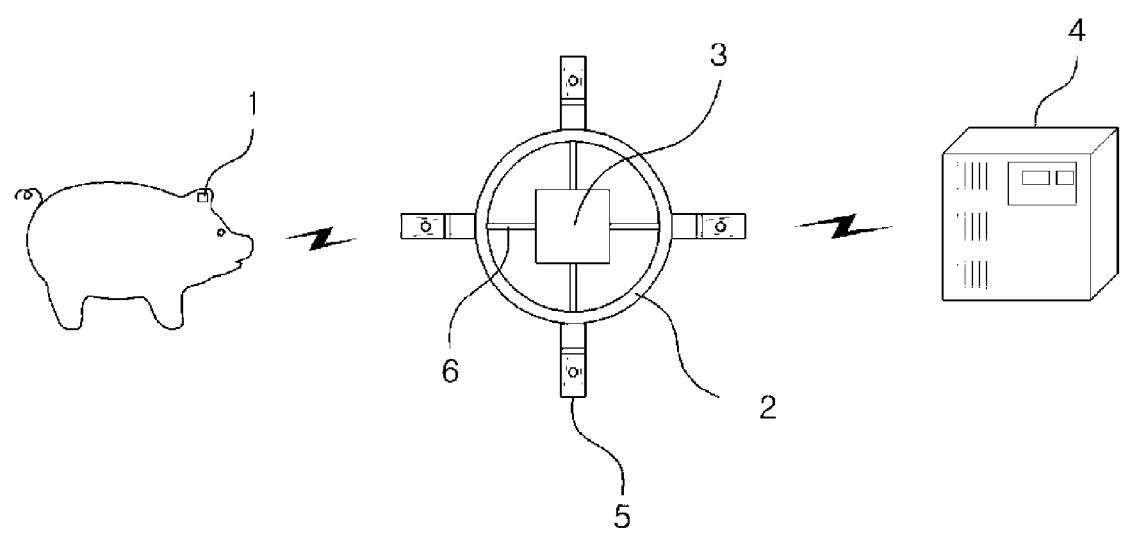
FIG. 1 is a view showing the configuration of an animal monitoring system according to an embodiment of the present invention.

The present invention will be hereafter described in detail with reference to the preferred embodiments and accompanying drawings of the present invention, assuming that elements having like functions will be denoted by like reference numerals.

When it is referred that a component "includes" another component in the detailed description or the claims of the present invention, it should be understood that this is not interpreted as being configured of only the corresponding component, but may further include other components, as far as an opposed description is not specially specified.

In addition, in the detailed description or claims, a component named as "~means", "~unit", "~module" or "~block" means a unit of processing at least one function or operation, and each of these may be implemented by software, hardware or a combination of these.

Hereinafter, an example of implementing a saliva test device and method, and an animal monitoring system and method using the same of the present invention will be described through a specific embodiment.

Meanwhile, in describing the present invention, a process of performing a saliva test on a pig among animals will be described for the convenience of explanation. That is, the present invention can be applied to all kinds of animals including livestock and pet animals.

FIG. 1 is a view showing the configuration of an animal monitoring system according to an embodiment of the present invention.

Referring to FIG. 1, an animal monitoring system of the present invention includes a chip 1 installed in a pig (animal), a saliva test device 3 installed in a water supply facility 2 to collect saliva from the pig (animal), test occurrence of a disease in real-time from the collected saliva, and transmit test result information to a management center, and the management center 4 for receiving and managing the test result information.

Here, the chip 1 preferably uses a short distance communication chip 1 and may use a Bluetooth chip or the like.

Meanwhile, in the saliva test device 3, an extruder 5 for supplying drinking water and collecting saliva may protrude at an end portion of the water supply facility 2, and a tube 6 for collecting saliva connects the extruder 5 and the saliva test device 3. In addition, the saliva test device 3 is preferably installed on the periphery of the water supply facility 2, and one saliva test device 3 may be connected to one water supply facility 2 or a plurality of water supply facilities 2. Meanwhile, the saliva test device 3 may perform functions, such as an automatic driving control, a drinking water supply control, a saliva collection control, a disease occurrence test control, a communication control and the like, in response to approach of the chip 1.

In the present invention configured like this, when the pig (animal) having the chip 1 installed therein approaches the saliva test device 3 within a predetermined distance, the saliva test device 3 is automatically driven. Apparently, the saliva test device 3 may maintain an all-time driving state. If it is sensed that the pig (animal) uses the water supply facility 2, the saliva test device 3 collects saliva from the mouth of the pig (animal). When collection of the saliva is finished, drinking water is supplied subsequently. Here, the process of collecting saliva and supplying drinking water may be randomly set, and therefore, the saliva may be collected after the drinking water is supplied, or the saliva may be collected while the drinking water is supplied.

Subsequently, the saliva test device 3 performs a disease occurrence test on the saliva in real-time. Subsequently, the saliva test device 3 informs the management center of test result information of each entity in real-time.

Figure 2:
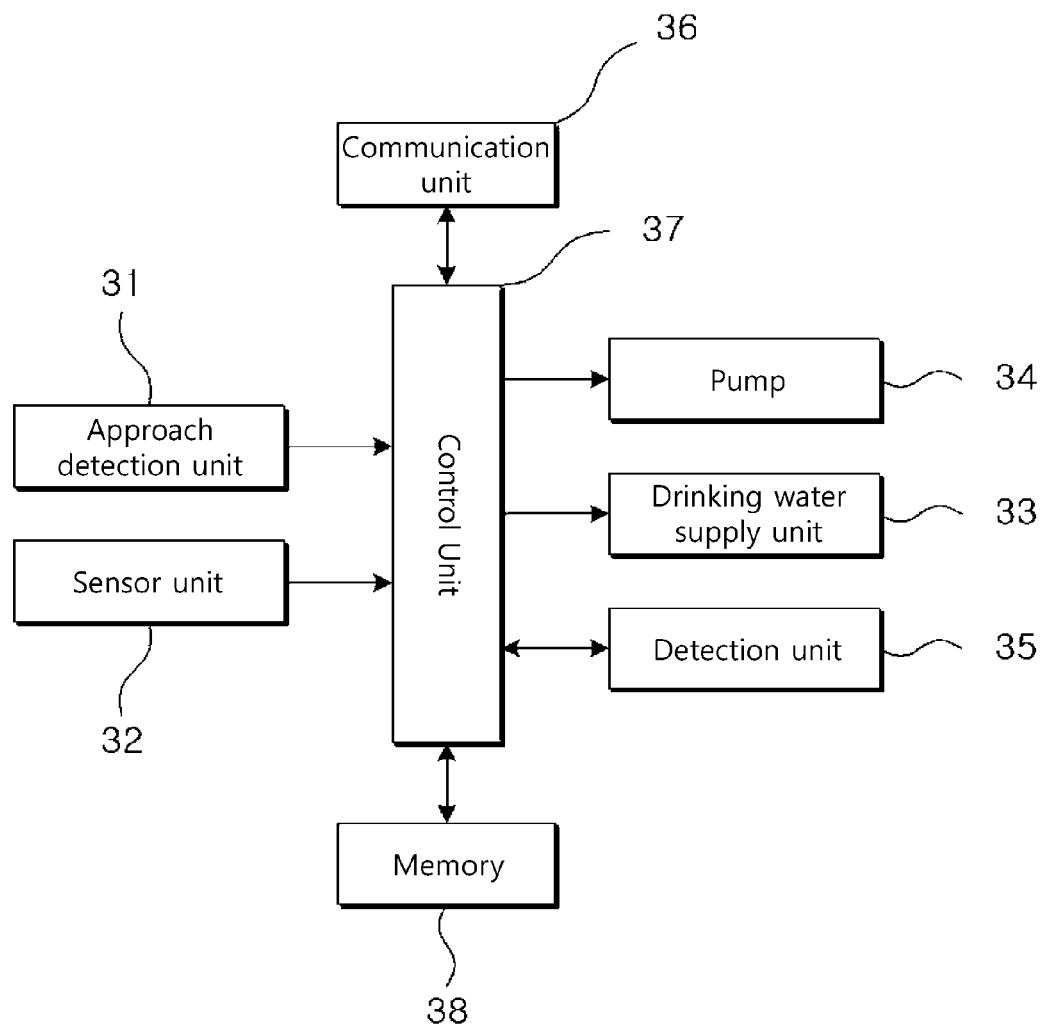
FIG. 2 is a view showing the configuration of a saliva test device according to an embodiment of the present invention.

FIG. 2 is a view showing the configuration of a saliva test device according to an embodiment of the present invention.

Referring to FIG. 2, the saliva test device 3 of the present invention includes: an approach detection unit 31 maintaining an all-time driving state to generate an approach detection signal in response to approach of the chip 1 within a predetermined distance; a sensor unit installed at an end portion of a drinking water pipe (21 of FIG. 4) to generate a contact detection signal in response to contact of a pig (animal); a drinking water supply unit 33 for controlling supply of drinking water in response to at least any one of the approach detection signal and the contact detection signal; a pump 34 connected to one end of a tube 6 installed at an end portion of the drinking water pipe 21 to suction and collect saliva in response to the contact detection signal; a test unit 35 for performing a disease occurrence test on the collected saliva and outputting test result information; a communication unit 36 for informing the management center 4 of the test result information; a control unit 37 for generating a system driving control signal in response to the approach detection signal, generating a pump driving control signal in response to the contact detection signal, generating a drinking water supply control signal in response to collection (amount) of the saliva, and performing transmission control on the test result information; and a memory 38 for storing an operation program and storing inputted and outputted data.

Here, the approach detection unit 31 preferably uses a short distance communication module and may use a Bluetooth module or the like as the short distance communication module.

The drinking water supply unit 33 preferably includes a solenoid valve (22 of FIG. 4) automatically opened and closed in response to the collection (amount) of the saliva.

The pump 34 preferably uses a peristaltic tubing pump 34. This may minimize stress of the pig (animal).

The communication unit 36 may be configured as a wired or wireless communication module and is preferably configured to be capable of wired and wireless communication with a computer (not shown) installed in a farm or the management center 4. Here, the communication unit 36 is preferably connected to the management center 4 by way of the computer installed in a farm.

In the saliva test device 3 of the present invention configured like this, the approach detection unit 31 generates and transmits an approach detection signal to the control unit 37 when the chip 1 approaches within a detection radius. The control unit 37 generates a system driving control signal in response to the approach detection signal and drives the system. Then, the sensor unit 32 is driven, and the sensor unit 32 determines whether there is a contact of a pig (animal). If a pig (animal) contacts an end portion of the drinking water pipe 21, the sensor unit 32 generates and transmits a contact detection signal to the control unit 37.

Then, the control unit 37 generates a pump driving control signal in response to the contact detection signal and drives the pump 34. Then, the pump 34 suctions saliva in the mouth of the pig (animal) through the tube 6 installed at an end portion of the drinking water pipe 21. The collected saliva is supplied to the test unit 35, and for example, if the collected amount of saliva reaches a predetermined amount, the test unit 36 generates and transmits a drinking water control signal to the control unit 37. Then, the control unit 37 controls supply of drinking water in response to the drinking water supply control signal. At this point, the process of collecting saliva and supplying drinking water may be randomly set as described above. Subsequently, the test unit 35 performs a disease occurrence test on the collected saliva. Then, the test unit 35 generates and transfers test result information to the control unit 37, and the control unit 37 performs transmission control to transmit the test result information to the management center 4 through the communication unit 36. Like this, in the present invention, a disease occurrence test is performed and test result information is informed in real-time through the saliva test device 3.

Figure 3:
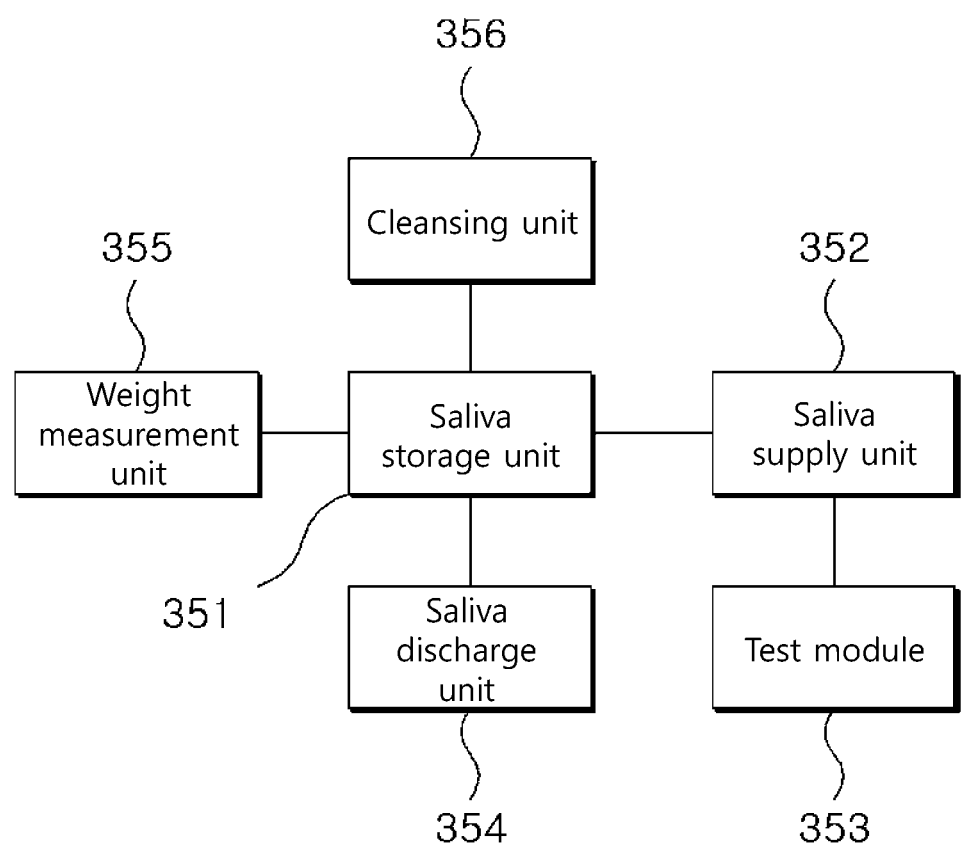
FIG. 3 is a view showing the configuration of a test unit according to an embodiment of the present invention.

FIG. 3 is a view showing the configuration of a test unit 35 according to an embodiment of the present invention.

Referring to FIG. 3, the test unit 35 of the present invention includes: a saliva storage unit 351 connected to the other end of the tube 6 to store collected saliva; a saliva supply unit 352 for supplying the stored saliva; a test module 353 for performing a disease occurrence test; and a saliva discharge unit 354 for discharging the saliva.

Here, the test unit 35 preferably further includes a weight measurement unit 355 for measuring the weight of the collected amount of saliva.

In addition, the test unit 35 preferably further includes a cleansing unit 356 for cleansing the saliva storage unit 351.

Meanwhile, the saliva supply unit 352 and the saliva discharge unit 354 preferably include a solenoid valve controlled by the control unit 37.

When the saliva is stored in the saliva storage unit 351 by driving the peristaltic tubing pump 34, the test unit 35 of the present invention configured like this collects saliva until the saliva reaches a predetermined amount in the saliva storage unit 351. At this point, if the saliva reaches a predetermined amount, the test unit 35 generates a pump drive stop signal for stopping operation of the peristaltic tubing pump 34. In response to the pump drive stop signal, the control unit 37 generates and provides a saliva supply signal to the test module 353. Then, the test module 353 performs a disease occurrence test in real-time. Meanwhile, if the disease occurrence test is completed, the test module 353 generates and transmits test result information and a disease occurrence test completion signal to the control unit 37. Then, the control unit 37 transfers the test result information to the communication unit 36 to transmit the test result information and controls to discharge the stored saliva to the outside through the saliva discharge unit 354 in response to the disease occurrence test completion signal. Then, a cleansing process may be performed for the saliva storage unit 351, and the cleansing liquid is discharged to the outside through the saliva discharge unit 354.

Meanwhile, here, collection of saliva may be performed for each pig (animal) or for all pigs (animals).

Figure 4:
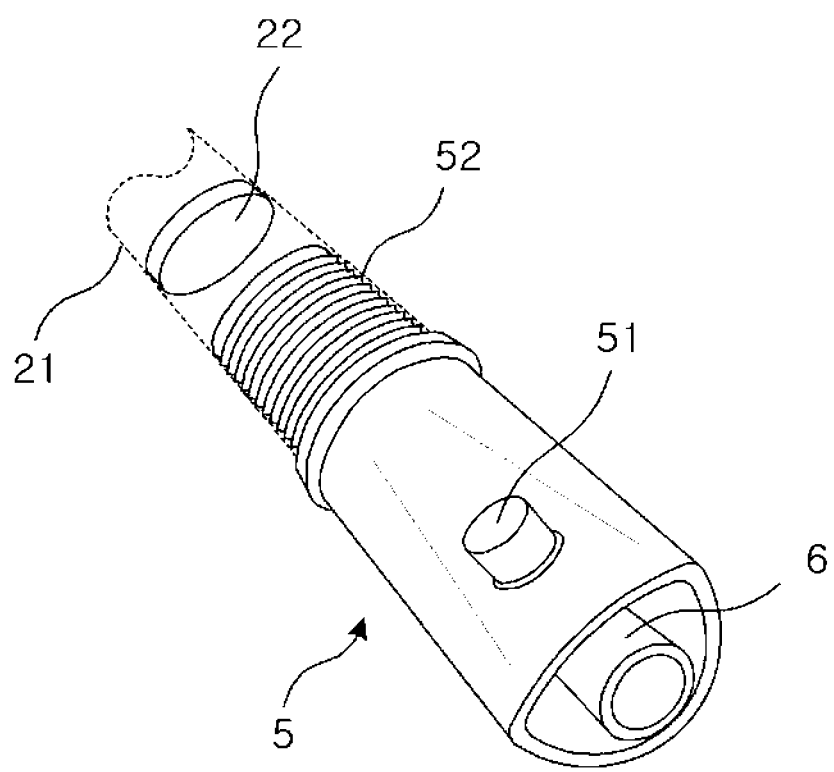
FIG. 4 is a view showing the configuration of an extruder according to an embodiment of the present invention.

FIG. 4 is a view showing the configuration of an extruder according to an embodiment of the present invention.

Referring to FIG. 4, the extruder 5 of the present invention is installed at an end portion of the drinking water pipe 21, and a button 51 that is opened in response to biting of a pig (animal) is formed.

Here, the extruder 5 is preferably manufactured as a part separated from the water supply facility 2, and thus a coupling unit 52 coupled to the water supply facility 2 may be further formed.

In addition, a fixing unit (not shown) for fixing the button 51 is formed inside the extruder 5, and a drinking water passage hole which is communicated by the vertical movement of a hole formed in the button 51 to pass drinking water and a tube hole through which the tube 6 connected to the peristaltic tubing pump 34 passes are formed in the fixing unit.

Meanwhile, the tube 6 connected to the peristaltic tubing pump 34 may be set while protruding toward the outside of the extruder 5.

In the extruder 5 of the present invention configured like this, drinking water is supplied to the extruder 5 in response to opening of the solenoid valve formed in the drinking water pipe 21 as described above (when the collected amount of saliva reaches a predetermined amount), and the drinking water passage hole is communicated by the biting action of the pig (animal), and thus the drinking water is supplied.

Then, a saliva test method of the present invention using the animal monitoring system configured as described above will be described.

Figure 5:
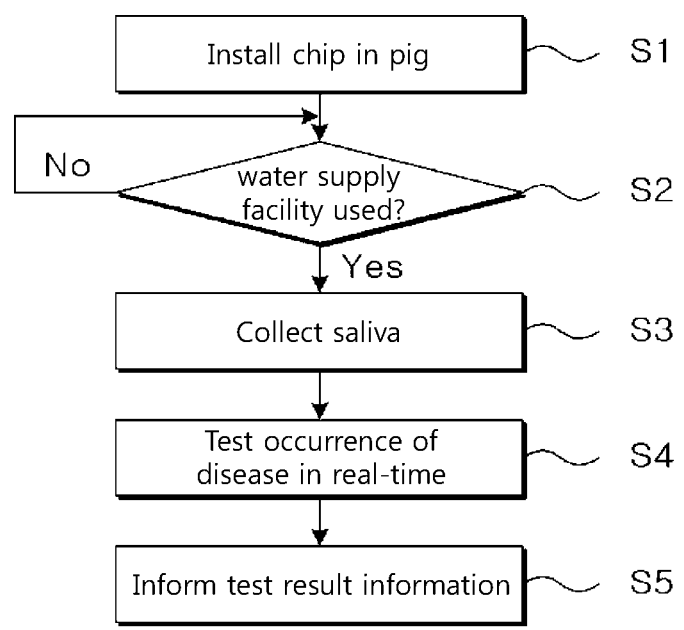
FIG. 5 is a flowchart illustrating an animal monitoring method according to an embodiment of the present invention.

FIG. 5 is a flowchart illustrating an animal monitoring method according to an embodiment of the present invention.

Referring to FIG. 5, first, a chip 1 is installed in a pig (animal) (step S1).

If the pig (animal) having the chip 1 installed therein uses the water supply facility 2 (step S2), the saliva test device 3 detects this and collects saliva (step S3) and subsequently performs a disease occurrence test on the saliva in real-time (step S4).

Meanwhile, the saliva test device 3 generates and informs test result information to the management center 4 (step S5). At this point, the test result information preferably includes information on an entity from which the saliva is collected, information on a result of analyzing occurrence of a disease, and an analysis time.

Figure 6:
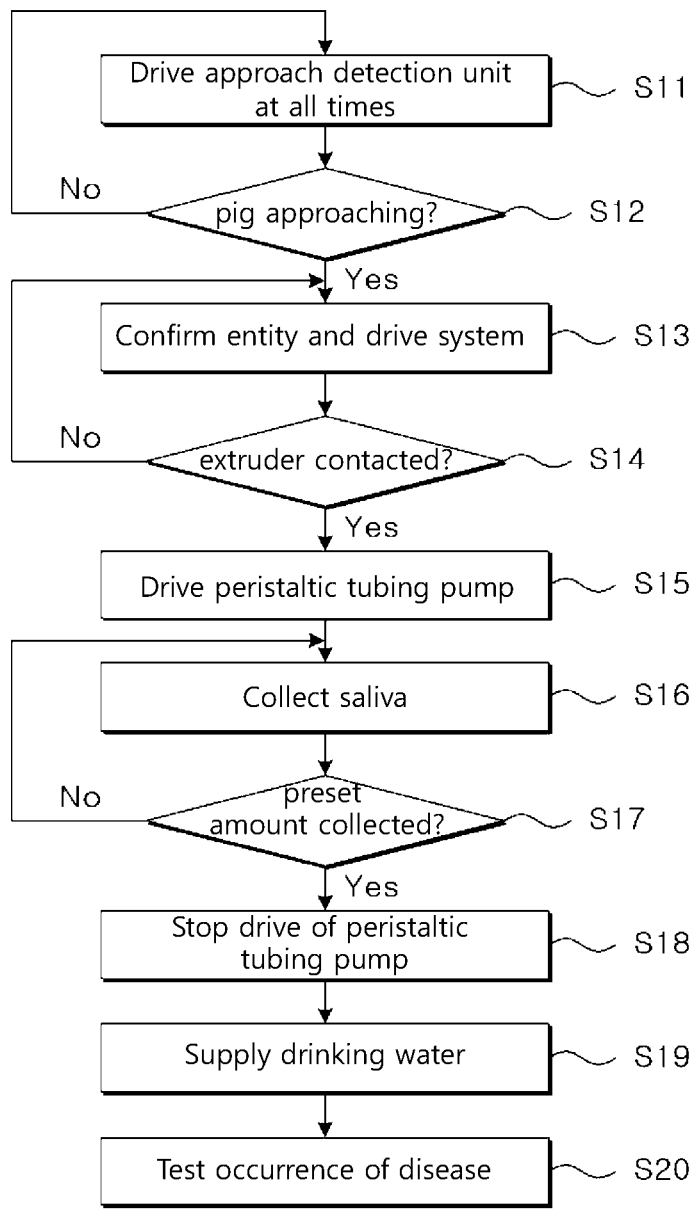
FIG. 6 is a flowchart illustrating a saliva test method according to an embodiment of the present invention.

FIG. 6 is a flowchart illustrating a saliva test method according to an embodiment of the present invention.

Referring to FIG. 6, while the approach detection unit is driven at all times (step S11), if a pig (animal) having a chip 1 installed therein approaches the water supply facility 2 (step S12), the approach detection unit 31 confirms and transfers the ID of the corresponding entity to the control unit 37 (step S13). In addition, the approach detection unit 31 generates and transfers an approach detection signal to the control unit 37, and the control unit 37 may drive all or part of the system (step S13).

In response to driving of the system, the sensor unit 32 determines whether the pig (animal) contacts with (bites) the extruder 5 (step S14).

When the pig (animal) bites the extruder 5, the sensor unit 32 generates and transmits a contact detection signal to the control unit 37. Then, the control unit 37 generates a pump driving control signal and drives the peristaltic tubing pump 34 in response to the contact detection signal (step S15). Therefore, saliva in the mouth of the pig (animal) is collected (step S16).

At this point, the test unit 35 determines whether the collected amount of saliva reaches a predetermined amount (step S17), and if the collected amount of saliva reaches a predetermined amount, the test unit 35 generates and transmits a peristaltic tubing pump drive stop signal and a drinking water supply control signal to the control unit 37 (step S18).

Then, the control unit 37 stops operation of the peristaltic tubing pump 34 and supplies drinking water by opening the solenoid valve installed in the drinking water pipe 21. Subsequently, as the drinking water passage hole is communicated according to biting of the pig (animal), drinking water is discharged (step S19).

Meanwhile, the collected saliva is supplied to the test unit 35, and a disease occurrence test is performed in real-time (step S20).

Then, the test unit 35 generates and transfers test result information to the control unit 37, and the control unit 37 performs transmission control to transmit the test result information to the management center 4 through the communication unit 36. Therefore, a disease occurrence test is performed and test result information is informed in real-time.

Figure 7:
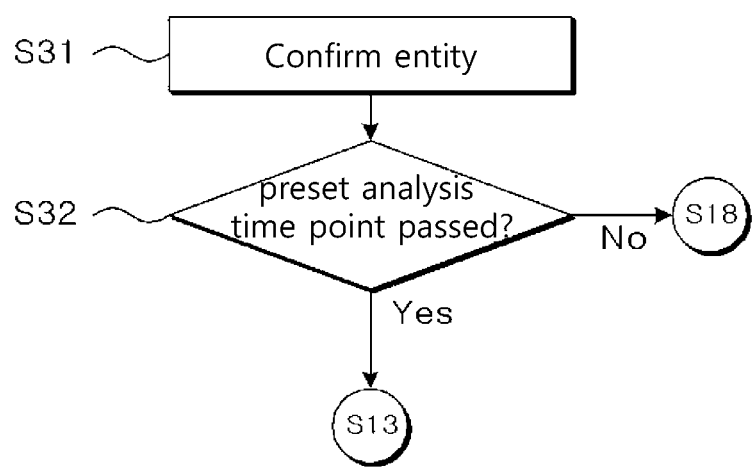
FIG. 7 is a flowchart illustrating a process of processing the same entity according to an embodiment of the present invention.

Meanwhile, when the same entity approaches again (step S31), as shown in FIG. 7, the control unit 37 confirms a disease occurrence analysis time of the corresponding entity and determines whether a set time is exceeded (step S32). If the set time is not exceeded, the peristaltic tubing pump 34 maintains the stopped state, and if a contact detection signal is generated, drinking water is supplied immediately by opening the solenoid valve through the drinking water supply unit 33 (proceeds to step S18). That is, the process proceeds to step S13 only when the disease occurrence analysis time exceeds the set time to perform the saliva collection process.

Meanwhile, when a plurality of salvia storage units 351 is provided in each extruder 5, the disease occurrence test may be simultaneously performed on a plurality of entities. That is, the salvia storage units 351 may be manufactured in a mobile type in accordance to the disease occurrence analysis time. In this case, when a large number of entities simultaneously use the extruder 5, it is preferable to use separate equipment, e.g., a camera or the like, to distinguish the entities from each other.

Meanwhile, although it is described in this embodiment that the drinking water is supplied after the saliva is collected, the saliva may be collected after the drinking water is supplied, or the saliva may be collected at the same time as the drinking water is supplied. A corresponding process is preferably determined according to the condition and environment of the antibody test.

Figure 8:
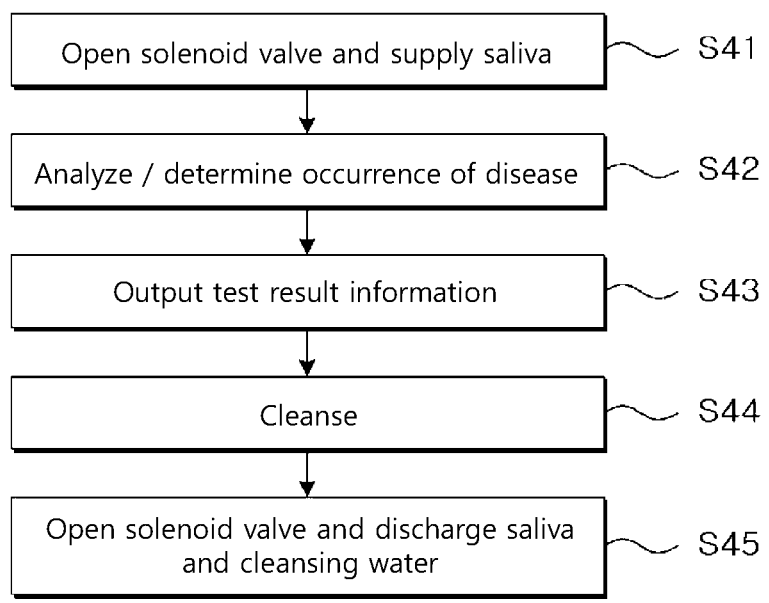
FIG. 8 is a flowchart illustrating a process of testing occurrence of a disease according to an embodiment of the present invention.

FIG. 8 is a flowchart illustrating a process of testing occurrence of a disease according to an embodiment of the present invention.

Referring to FIG. 8, the saliva stored in the saliva storage unit 351 is provided to the test module 353 by opening the solenoid valve (step S41).

Then, the test module 353 analyzes the saliva and determines occurrence of a disease (step S42) and outputs test result information as a result thereof (step S43).

Meanwhile, the inside of the saliva storage 351 may be cleansed by the cleansing unit 356 (step S44), and the saliva and cleansing liquid remaining inside the saliva storage 351 may be discharged to the outside by opening the solenoid valve of the saliva discharge unit 354 (step S45).

The technical spirit of the present invention has been described above through some embodiments.

It is apparent that those skilled in the art may diversely modify or change the embodiments described above from the description of the present invention. In addition, although it is not explicitly shown or described, it is apparent that those skilled in the art may make various forms of modifications including the spirit of the present invention from the description of the present invention, and this still falls within the scope of the present invention. The embodiments described above with reference to the accompanying drawings are described for illustrative purposes, and the scope of the present invention is not limited to the embodiments.

The invention claimed is:

1. A saliva test device comprising:
   a means for generating an approach detection signal;
   a means for generating a contact detection signal;
   a drinking water supply unit for controlling supply of drinking water in response to at least any one of a plurality of approach detection signals and contact detection signals;
   a pump connected to one end of a tube installed at an end portion of a drinking water pipe to suction and collect saliva in response to the contact detection signal;
   a test unit for performing a disease occurrence test on the collected saliva and outputting test result information;
   a communication unit for informing a management center of the test result information;
   a control unit for generating a system driving control signal in response to the approach detection signal, generating a pump driving control signal in response to the contact detection signal, generating a drinking water supply control signal in response to collection of the saliva, and performing transmission control on the test result information; and
   a memory for storing an operation program and storing inputted and outputted data.

2. The device saliva test according to claim 1, wherein the test unit includes:
   a saliva storage unit connected to the other end of the tube to store the collected saliva;
   a saliva supply unit for supplying the stored saliva;
   a test module for performing a disease occurrence test; and
   a saliva discharge unit for discharging the saliva.

3. The saliva test device according to claim 1, wherein the pump is a peristaltic tubing pump.

4. A saliva test method comprising the steps of:
   driving a system in response to generation of an approach detection signal;
   collecting saliva from a mouth of a corresponding animal by driving a peristaltic tubing pump in response to generation of a contact detection signal;
   generating a peristaltic tubing pump drive stop signal and a drinking water supply control signal and providing drinking water when the collected saliva reaches a predetermined amount;
   supplying the collected saliva to a test unit and performing a disease occurrence test in real-time;
   generating and outputting test result information of the disease occurrence test; and
   informing a management center of the test result information.

5. The saliva test method according to claim 4, wherein a solenoid valve installed in a drinking water pipe is opened in response to the drinking water supply control signal.

* * * * *